United States Patent [19]

Stanwich et al.

[11] Patent Number: 5,181,755
[45] Date of Patent: Jan. 26, 1993

[54] SMALL OBJECT HANDLING DEVICE, ASSEMBLY AND METHOD OF MANUFACTURE

[75] Inventors: Lawrence J. Stanwich, Wellesley; Kenneth J. Berk, Newton; Fredrick M. Berk, Brookline; Donald A. Berk, Newton, all of Mass.

[73] Assignee: Pulpdent Corporation, Watertown, Mass.

[21] Appl. No.: 651,997

[22] Filed: Feb. 7, 1991

[51] Int. Cl.$^5$ ............................................... B66C 1/00
[52] U.S. Cl. ...................................... 294/1.1; 206/104
[58] Field of Search ................... 294/1.1; 206/99, 104; 15/104 A, 104.94

[56] References Cited

U.S. PATENT DOCUMENTS

| | | | |
|---|---|---|---|
| 939,476 | 11/1909 | Copp | 294/1.1 X |
| 2,023,884 | 12/1935 | Grote | 206/104 X |
| 2,042,584 | 6/1936 | Bustamante | 206/104 X |
| 4,073,530 | 2/1978 | Seidler | 294/1.1 X |
| 4,600,227 | 7/1986 | Ennis et al. | 294/1.1 |
| 4,653,789 | 3/1987 | McWilliams et al. | 294/1.1 |
| 4,714,160 | 12/1987 | Bennett | 206/104 X |
| 4,953,902 | 9/1990 | Brown | 294/1.1 |

FOREIGN PATENT DOCUMENTS 852053 10/1952 Fed. Rep. of Germany ....... 294/1.1

Primary Examiner—Johnny D. Cherry
Assistant Examiner—Dean J. Kramer

[57] ABSTRACT

A small object handling device composed of an elongated rod with a wax composition coated over one end thereof. The invention further comprises an assembly of small object handling devices, with each composed of an elongated rod having a pressure sensitive adhesive composition coated over one end, and with the opposite end connected to a common rack. A flexible strip may cover the common rack and rods to protect the pressure sensitive adhesive ends of said rods and to provide a matchbook-like appearance. In an alternate embodiment, the device has a tubular member filled with pressure sensitive adhesive, with a rod adjustably coupled to one end of the member for forcing the pressure sensitive adhesive out from the opposite end. The method of the invention involves dipping each rod into a liquid bath of pressure sensitive adhesive at a maximum temperature of no more than 140 percent of the melting temperature of the pressure sensitive adhesive, removing each rod from the liquid bath with a coating of pressure sensitive adhesive surrounding the immersed end, and allowing the coating to cool and harden on the rod.

1 Claim, 1 Drawing Sheet

SMALL OBJECT HANDLING DEVICE, ASSEMBLY AND METHOD OF MANUFACTURE

FIELD OF THE INVENTION

This invention relates to a device for picking up, holding, and positioning small solid objects and, more particularly, to a device especially adapted for use in the dental or medical profession to hold small solid objects in place without fear of dropping or losing the object in the operatory site, and to an assembly of removable small object handling devices and method of manufacture.

BACKGROUND OF THE INVENTION

In certain fields such as dentistry, the operating site is small and confined, making it difficult to hold and/or position small solid objects in a desired alignment in preparation for or subsequent to an operatory procedure. This is equally true for many medical procedures, and in the field of electronics and watch repair. Moreover, the widespread use of gloves, by dental practitioners in particular, has made it increasingly more difficult to work with and hold small objects. The use of gloves reduces the tactile feel and sense of security in holding, handling and working with small solid objects in a confined space. This is further aggravated by the fear of the dentist or dental practitioner of losing the small object intra-orally, which can result in the patient swallowing or aspirating the object. The latter can result in a life-threatening, clinical situation. Accordingly, the use of gloves in performing dental and/or medical procedures has created a strong need for a device to assist the dental or medical practitioner in handling, picking up, and/or placing small solid objects into and out of the operatory site. This same need exists in other fields, particularly electronic assembly, watch repair, and general household use. The small solid object can represent an inlay, veneer, orthodontic bracket, or any metallic or non-metallic member or abutment which requires alignment. Currently, tweezers are often used for this purpose and require agility and care to avoid dropping the part, and are limited in alignment possibilities.

OBJECTS OF THE INVENTION

It is, accordingly, an object of the present invention to provide a device for working with small, delicate, hard-to-handle, solid objects, and more particularly, to facilitate picking up, handling, and placement of such objects. It is a further object of the present invention to provide a method for manufacturing the holding device of the present invention.

SUMMARY OF THE INVENTION

The small object handling device of the present invention comprises an elongated rod having a coating of a pressure sensitive adhesive composition surrounding one end thereof and uniformly extending over the sides adjacent said end. A "pressure sensitive adhesive" is defined as a material which in dry form is aggressively and permanently tacky at room temperature, and firmly adheres to a variety of dissimilar surfaces upon mere contact without the need for more than finger or hand pressure. Tack or tackiness is the property of a material which enables it to form a bond of measurable strength immediately on contact with another surface. The preferred pressure sensitive adhesive of the present invention is a wax composition, although other pressure sensitive adhesive formulations may be used, as will be discussed in detail later in the specification.

The assembly of small object handling devices of the present invention comprises:

a support rack;

a multiplicity of elongated rods with each rod having one end thereof connected to said support rack, such that each rod may be readily broken off for independent use, and an opposite unconnected end; and a coating of a pressure sensitive adhesive composition surrounding the unconnected end thereof and uniformly extending over the sides adjacent said unconnected end.

The method of the present invention comprises the steps of introducing one end of an elongated rod into a liquid bath composed of a pressure sensitive adhesive composition, maintaining the bath at a temperature above the melting temperature of the pressure sensitive adhesive composition and up to a maximum temperature of 140 percent of the melting temperature, and removing the rod to form a coating of solidified pressure sensitive adhesive surrounding the immersed end and uniformly extending over the sides adjacent said end. This process may be repeated one or more times to obtain the coating thickness and configuration desired. Alternately, the pressure sensitive adhesive formulation may form a liquid bath due to the presence of a solvent. Upon removal of each rod from the liquid bath, with a coating of pressure sensitive adhesive surrounding the immersed rod, the solvent is allowed to evaporate, allowing the coating to harden on the rod. This process may be repeated one or more times to obtain the coating thickness and configuration desired.

Another embodiment of the present invention is directed to a device for handling very small solid objects comprising a hollow member having opposite ends, a pressure sensitive adhesive composition disposed within said hollow member, and an elongated rod adapted to be coupled to said hollow member at one of said opposite ends for manually forcing said pressure sensitive adhesive composition out from said open end upon advancing said rod through said member.

BRIEF DESCRIPTION OF THE DRAWINGS

Further objects and advantages of the present invention will become apparent from the following detailed description of the invention when read in conjunction with the accompanying drawings of which.

DETAILED DESCRIPTION OF THE INVENTION

Figure 1:
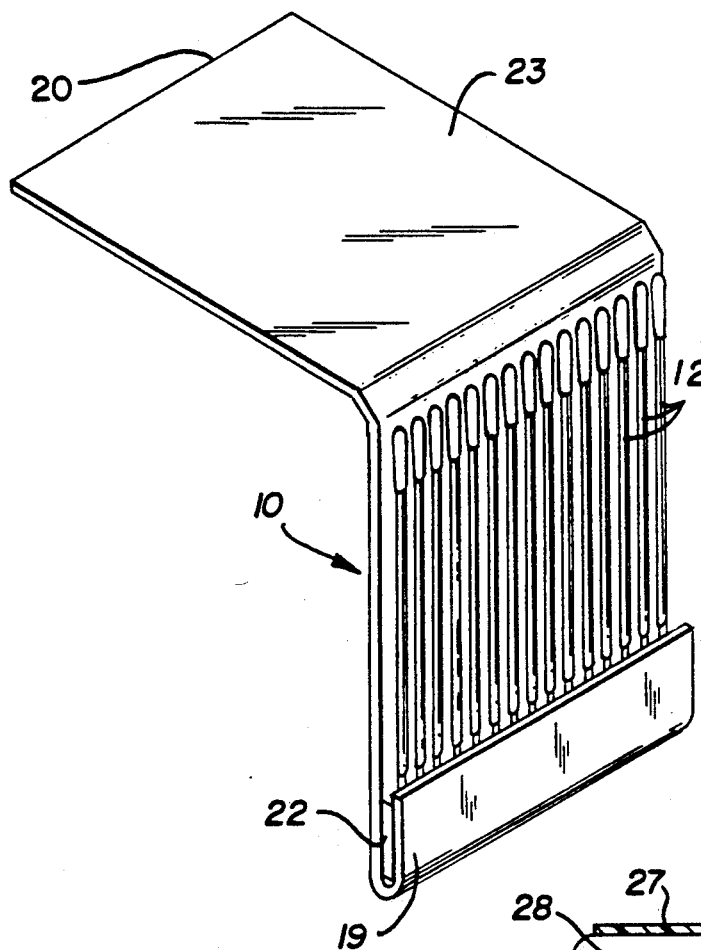
FIG. 1 is a view in perspective of the preferred embodiment of the present invention.
Figure 3:
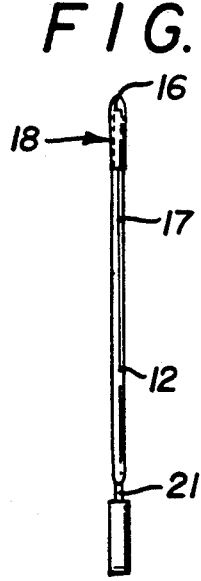
FIG. 3 is an end view taken along the line 3—3 of FIG. 2.
Figure 2:
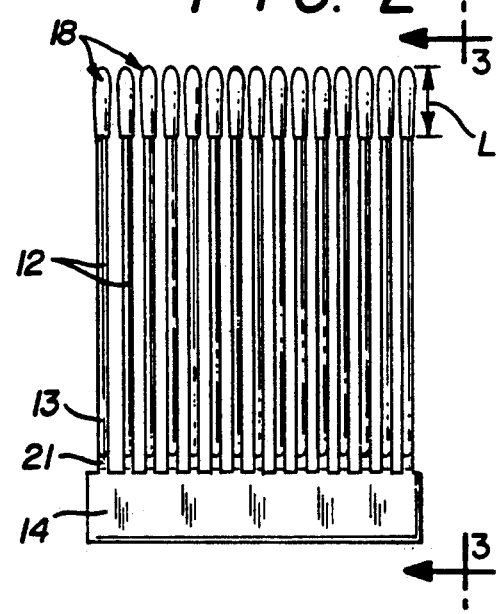
FIG. 2 is another view in perspective of the assembly of FIG. 1 with the outer cover removed.

FIGS. 1, 2, and 3, inclusive, illustrate the preferred embodiment of the present invention. The assembly (10) comprises a multiplicity of individual, elongated, generally cylindrical, rods (12) each having one end (13) connected to a common support rack (14), and an opposite unconnected end (16) covered with a pressure sensitive adhesive coating (18), which surrounds the unconnected end (16) and provides an evenly distributed coating of pressure sensitive adhesive around the side surface (17) contiguous to the unconnected end (16). The rack (14) is connected to one end (19) of a flexible strip (23), which is folded over the rack (14) and the rods (12) to protect the pressure sensitive adhesive coated unconnected ends (16), and to provide the appearance and look of a "matchbook." The pressure sensitive adhesive coating (18) on the unconnected end (16) of each rod (12) is used in accordance with the present invention to pick up and hold an object of small size.

The array of rods (12) are arranged in parallel to form a single row extending from the common rack (14). The rods (12) may be of any suitable geometry and length, and may be composed of wood, metal or plastic. An elastomeric resin composition is preferred for both the rods (12) and base (14), so that they may be formed in a single, unitary operation by, for example, injection molding.

The rods (12) are connected to the common rack (14) at a connection point (21). The connection point (21) is the fulcrum, permitting each rod to be readily broken off from the rack (14) with little effort. The strip (23) is preferably a paper pulp product, such as cardboard, having one end (19) folded over the lower end (22) of the rack (14) to form a "U"-shaped configuration, and having an opposite free end (20). The folded over end (19) is connected or bonded to the rack (14), with the opposite open end (20) adapted to fit into the "U"-shaped fold. The strip (23) should be long enough to provide a "matchbook"-like appearance when folded over.

The pressure sensitive adhesive coating (18) formed over the unconnected end (16) of each rod (12) should possess a degree of tackiness, so that it will stick to any metallic or non-metallic object upon contact, and preferably without leaving a residue upon separation from the object. Although any pressure sensitive adhesive formulation may be used, a natural or organic wax composition is preferred. A tackifier may be added to enhance or control the degree of tack. Tackifiers of importance include wood rosins or rosin acids, rosin esters (typically of glycerol or pentaerythritol), modified rosin esters, including hydrogenated types, polyterpenes derived from the pinenes in wood turpentine, terpene-phenolics, phenol-formaldehyde resins, alpha-methylstyrene polymers, vinyl toluene polymers, coumarone-indene resins, amorphous polypropylene, etc., as well as the most widely used type: hydrocarbon resins. The latter are made by oligomerization of $C_5$ and $C_9$ unsaturated petroleum fractions.

Alternate pressure sensitive adhesives may be formed from a natural or butyl or styrene copolymer rubber, elastomers, silicone gum, ethylene-vinyl acetate copolymers, individually or mixed with tackifiers as above identified. Also acrylics can be used.

Typical formulations for tackified elastomers:

| 1. | milled pale crepe (NR) | 100 |
| --- | --- | --- |
|  | polyterpene (MW 750) | 90 |
|  | solvent to obtain proper viscosity (hexane/toluene mixture) |  |
| 2. | Kraton 1107 | 100 |
|  | hydrogenated rosin ester (s.p. 104 degrees Centigrade) | 84 |
|  | liquid hydrogen rosin ester solvent (e.g., toluene) | 37 |
| 3. | PIB (MW 2 million) | 100 |
|  | PIB (MW 1200) | 70 |
|  | liquid hydrogen rosin ester | 35 |
|  | $C_5$ hydrocarbon resin (s.p. 100 degrees Centigrade) | 45 |
|  | solvent (e.g., heptane) |  |

The length and diameter of the rods (12), the number of rods (12) and the thickness of the pressure sensitive adhesive coating (18) are variables which are selected for a particular field of application. The geometry of the pressure sensitive adhesive coating (18) may be uniformly cylindrical or conical, with the coated length ("L") surrounding the side (17) dependent upon the depth of insertion of the rods (12) into a liquid bath of a pressure sensitive adhesive formulation. When wax is used, the liquid bath should be held to a temperature above the melting temperature of the wax composition, but not more than 140 percent of such maximum temperature, such that upon removal from the bath each rod will quickly solidify, leaving a coating on the side surface (17) of uniform thickness. This dipping process may be repeated one or more times to obtain the coating thickness and configuration desired.

Figure 4:
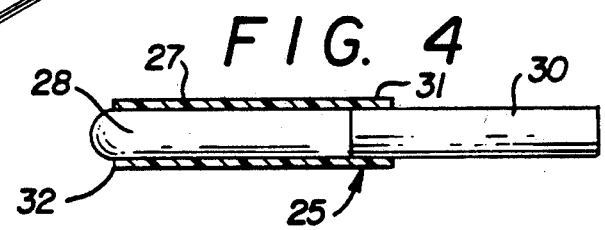
FIG. 4 is a view, in longitudinal section, of an alternate embodiment of the present invention.

An alternative embodiment of the present invention is shown in FIG. 4. The device (25) comprises a hollow tubular member (27) filled with a composition of pressure sensitive adhesive (28) of equivalent composition to the pressure sensitive adhesive coating (18) of FIGS. 1-3. A solid rod (30) is adjustably coupled to one end (31) of the tubular member (27). The coupling may be formed simply by the physical insertion of the rod (30) or a threadable connection (not shown). The solid rod (30) has a diameter smaller than the diameter of the tubular member (27), so as to facilitate advancing the pressure sensitive adhesive composition (28) until it sticks partially out of the free end (32). The stickout length of the pressure sensitive adhesive beyond the free end (32) is readily increased by advancing the rod (30) further into the tubular member (27). After use, the exposed section of pressure sensitive adhesive may be discarded, permitting the device (25) to be reused a number of times for different applications.

The tubular member (27) may be formed by dividing an endless length of tubing filled with pressure sensitive adhesive into multiple sections (27) of predetermined length.

What I claim is:

1. Assembly of small object handling devices, comprising: a support rack; a multiplicity of elongated rods, with each rod having a round cross-section and having one end thereof connected to said support rack, such that each rod may be readily broken off for independent use, and an opposite unconnected end; and a coating of a pressure sensitive adhesive composition surrounding the unconnected end thereof, and uniformly extending over the sides adjacent said unconnected end, with said pressure sensitive adhesive composition consisting essentially of wax and a tackifier, with the tackifier selected from the group consisting of wood rosins, rosin acids, rosin esters, polyterpenes, terpene-phenolics, phenol-formaldehyde resins, alpha-methylstyrene polymers, vinyl toluene polymers, coumarone-indene resins, amorphous polypropylene, hydrocarbon resins having between $C_5$ and $C_9$ carbon atoms, natural or butyl or styrene copolymer rubber, silicone gum, and ethylenevinyl acetate copolymers; further comprising a flexible strip having one end connected to said rack, and an opposite free end for folding over and protecting said rods, and to provide a matchbook-like appearance.

* * * * *